United States Patent [19]

Ogle, II

[11] Patent Number: 5,065,783

[45] Date of Patent: Nov. 19, 1991

[54] VALVE WITH SELF-SEALING INTERNAL CANNULA

[75] Inventor: George B. Ogle, II, 5616 Bonita, Alta Loma, Calif. 91701

[73] Assignee: George Braddock Ogle, II, Alta Loma, Calif.

[21] Appl. No.: 585,397

[22] Filed: Sep. 20, 1990

[51] Int. Cl.⁵ .............................................. A61M 5/32
[52] U.S. Cl. .............................. 137/68.1; 137/614.21; 251/149.7; 604/413; 604/905
[58] Field of Search .......................... 137/68.1, 614.21; 251/149.7; 604/244, 246, 249, 413, 905

[56] References Cited

U.S. PATENT DOCUMENTS

| | | | |
|---|---|---|---|
| 3,127,892 | 4/1964 | Bellamy, Jr. et al. | 604/905 X |
| 4,004,586 | 1/1977 | Christensen et al. | 604/413 |
| 4,080,965 | 3/1978 | Phillips | 137/68.1 X |
| 4,116,196 | 9/1978 | Kaplan et al. | 604/905 X |
| 4,169,475 | 10/1979 | Genese | 604/905 X |
| 4,181,140 | 1/1980 | Bayham et al. | 604/249 X |
| 4,219,221 | 8/1980 | Webb | 604/244 |
| 4,935,010 | 6/1990 | Cox et al. | 604/905 X |

*Primary Examiner*—John Rivell
*Attorney, Agent, or Firm*—Christie, Parker & Hale

[57] ABSTRACT

A valve insert includes an elongated cannula with first and second sharp ends. First and second elongated, flexible, elastomeric covers are respectively disposed over the first and second sharp ends of the cannula. Each cover is secured to an intermediate part of the cannula and is made of a material penetrable by the sharp ends of the cannula as the cannula moves longitudinally relative to the covers. The insert is mounted in an elongated bore through a valve body so that when a hypodermic syringe nozzle is inserted inito one end of the bore, the cannula and covers are displaced longitudinally, causing the sharp ends of the cannula to pierce the covers and open the cannula for fluid flow.

23 Claims, 1 Drawing Sheet

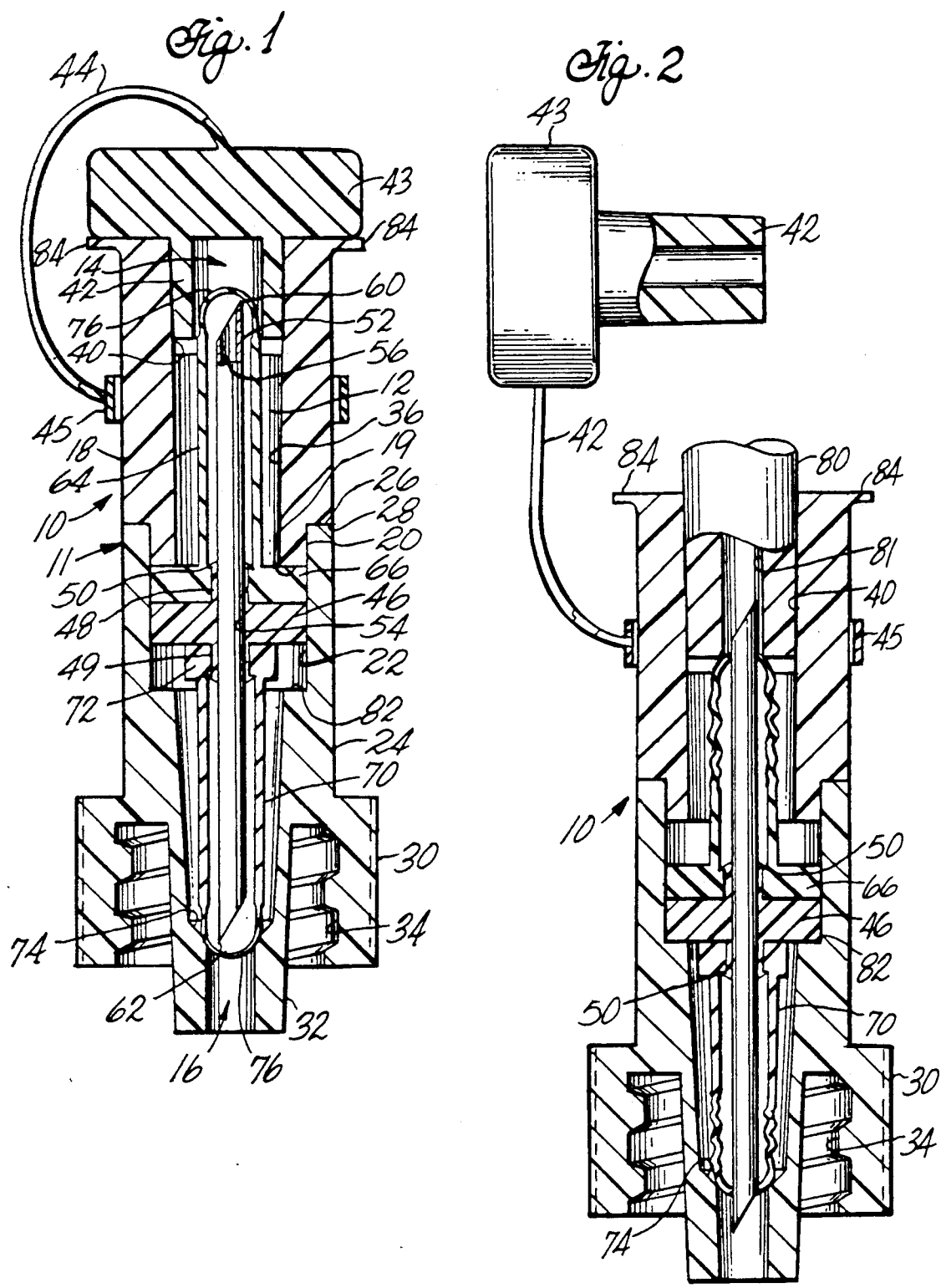

VALVE WITH SELF-SEALING INTERNAL CANNULA

BACKGROUND OF THE INVENTION

This invention relates to valve inserts and valves used to control intravenous flow of liquid to or from a patient.

It is common medical practice to insert an indwelling catheter into the vein of a patient, and tape the inserted catheter to the patient. The end of the catheter projecting from the patient carries a fitting which prevents the loss of blood, and permits medication to be administered to the patient, or blood samples to be taken from the patient, without requiring repeated puncturing of the patient. Such fittings are referred to as "intermittent caps" because they close the outer end of the indwelling catheter to prevent loss of blood from the patient, and yet permit intermittent intravenous access to the patient, as required.

The disadvantage of prior art intermittent caps, such as that shown in U.S. Pat. No. 4,083,916 to Raines (1987), is that they have relatively large flow paths open to contaminants when the caps are not in use. Such prior art caps are difficult, if not impossible, to sterilize immediately prior to each time medication is to be administered through them.

U.S. Pat. No. 3,500,821 to Ogle (1970) discloses blood sampling apparatus with aspiration means in which one end of a sharp-pointed cannula is covered by a rubber tube which permits blood to flow between the cannula exterior and tube interior when the device is in a patient and no blood sample is being taken.

SUMMARY OF THE INVENTION

This invention provides an improved valve insert, and an improved valve which can be connected to the outer end of an indwelling catheter, and which has a fluid flow path that is automatically kept closed, except when activated to permit fluids to pass through the valve. This minimizes the opportunity for contamination of the fluid flow path. Moreover, the valve of this invention can easily be sterilized just before each time fluid is to flow through it.

Briefly, the valve insert of this invention includes an elongated cannula with first and second sharp ends. First and second elongated, flexible, resilient, elastomeric covers are respectively disposed over the first and second sharp ends of the cannula. Each cover is secured to an intermediate part of the cannula to form a separate respective closed envelope over a respective sharp end. The covers are made of a material which is penetrable by the sharp ends of the cannula as the cannula moves longitudinally relative to the covers.

The preferred valve of this invention includes an elongated body with a bore extending longitudinally through it to form an inlet at one end and an outlet at the other end. The covered cannula is disposed in the bore to be movable longitudinally relative to the body. The cannula is also disposed with the first sharp end and cover adjacent the bore inlet and with the second sharp end and second cover adjacent the bore outlet. Means are provided for differentially limiting the travel of the cannula and second cover in a direction toward the inlet when a tubular element enters the inlet and pushes the first cover and cannula toward the outlet to cause each sharp point to penetrate the respective surrounding cover.

In the preferred form of the invention, a disk is secured around an intermediate part of the cannula exterior, and the first and second covers are each secured to respective first and second hubs on the disk, which extends outwardly and makes a close sliding fit in the bore of the body. A first internal shoulder in the valve bore limits the travel of the disk toward the inlet, and preferably includes a valve seat. Preferably, the first cover includes an outwardly extending flange formed integrally with the cover and secured around the first hub to serve as a washer or gasket against the valve seat. The outer periphery of the flange makes a sliding seal against the interior surface of the bore when the disk moves longitudinally in the body.

Preferably, the body includes a second internal shoulder which receives the end of the second cover over the second sharp end of the cannula to limit the travel of the second cover toward the body outlet.

In the preferred form of the invention, the bore at the inlet end of the body is tapered outwardly toward the inlet end to receive the tapered nozzle of a standard hypodermic syringe or other tubular element, such as a tapered connection from an intravenous set, which, when inserted into the bore inlet, engages the end of the first cover over the first sharp end of the cannula and forces the covered cannula toward the outlet end of the bore so that each sharp end of the cannula pierces the adjacent portion of the respective cover over it to open the cannula for fluid flow through it.

BRIEF DESCRIPTION OF THE DRAWINGS

FIG. 1 is a longitudinal sectional view of the presently preferred valve in the closed position; and FIG. 2 is a view similar to FIG. 2 showing the valve opened by insertion of the nozzle of a hypodermic syringe.

DESCRIPTION OF THE PREFERRED EMBODIMENTS

Referring to FIG. 1, a valve 10 includes an elongated, cylindrical body 11 with an elongated bore 12 extending through it to form an inlet end 14 and an outlet end 16.

For ease of construction and assembly, the valve body 11 includes an elongated, cylindrical inlet body section 18 of reduced external diameter at an inner end 19 remote from the inlet 14 to form a relatively short tubular segment 20 which makes a snug friction fit in a cylindrical bore 22 of an outlet body section 24, having an inner end 26 remote from the outlet end of the valve. The end 26 abuts an outwardly extending annular shoulder 28 formed at the juncture of segment 20 and the rest of the inlet body section 18. The two body sections may be of any suitable plastic material, but preferably are of a clear plastic for ease of inspection, and so the two body sections can be bonded together with glue or by spin-welding. Examples of suitable plastics are ABS, polyethylene, polypropylene, and acrylic.

An annular conventional Luer-lock collar 30 surrounds the outlet end of the valve body, the exterior of which is tapered inwardly away from the valve inlet to provide a standard tapered nozzle 32 identical with the nozzles found on conventional hypodermic syringes. The Luer-lock collar 30 includes the usual internal threads 34 for mating with external ears or threads (not shown) on the outer end of an indwelling catheter (not shown).

The longitudinal bore 12 extending through the outlet body section includes a cylindrical segment 36 which extends from the inner end of the outlet body section to about ⅔ of the distance to the outer end of the outlet body section where it merges with an outwardly extending tapered socket 40, which receives a tubular plug 42 with an external taper to match that of the socket. A closure 43 is formed integrally with the tubular plug 42, both of which may be made of the same plastic used for the valve body. The closure and tubular plug are secured by a tether cord 44 formed integrally at one end with the closure and at the other end with a ring 45 around the exterior of the valve body inlet section.

A disk 46, which may be made of the same plastic used for the valve body, makes a close sliding fit within bore 22. A first hub 48, formed integrally with the central portion of the disk, extends toward the inlet end of the valve, and a second hub 49, formed integrally with the central portion of the disk, extends toward the outlet end of the valve. The outer end of each hub includes a respective annular barb 50.

An elongated cylindrical cannula 52 makes a snug fit in a central bore 54 through the disk and hubs, and is coaxially disposed within the bore 12 that extends through the valve. The cannula is secured to the disk and hubs by suitable glue (not shown), and includes a passageway 56 through it to form a flow path for fluids through the valve.

The cannula includes a first sharp point 60 adjacent the inlet end of the valve and a second sharp point 62 adjacent the outlet end of the valve. A first elongated, flexible, resilient cover 64 (preferably made of rubber) is disposed over the first sharp end 60 of the cannula, and extends inwardly to terminate with an integrally formed, outwardly extending rubber flange 66, the outer periphery of which makes a sliding seal against bore 22 of the outlet body section to isolate the annular space surrounding the first cover from the annular space surrounding the second cover. The isolation is further effected by the rubber flange bearing against the inner end 19 of the inlet body section 18, when the valve is in the closed position (FIG. 1). The inner periphery of rubber flange 66 makes a tight stretch fit over the barb 50 on the first hub of the disk so the rubber flange and cover are held firmly in place as the disk and flange reciprocate in bore 22.

A second elongated, flexible, resilient cover 70 (preferably of rubber) is disposed over the second sharp end of the cannula and extends inwardly to terminate in an integrally formed, outwardly extending flange 72, which makes a tight stretch fit over the barb 50 on the second hub of the disk so the second cover is securely fastened to the disk as the disk reciprocates in bore 22. The outer end of the second cover rests in an internal shoulder 74, which tapers inwardly toward the valve outlet so the second cover is restrained from moving toward the valve outlet as the disk reciprocates in bore 22.

The outer end of each cover includes a respective section 76 of reduced thickness compared to the wall thickness of the rest of the cover to facilitate puncturing of the ends of the covers by the sharp ends of the cannulas, as described below with respect to FIG. 2. For example, the wall thickness of the end of each cover may be about 0.050", and the wall thickness of the adjacent part of each cover may be about 0.057".

FIG. 2 shows the intermittent cap open for fluid flow through the cannula. The tubular plug 42 is removed from the tapered socket 40, and a tubular element 80, such as the nozzle of a hypodermic syringe (not shown) or tapered end of an intravenous set (not shown) is inserted into the tapered socket to contact the outer end of the first cover and push the first cover, cannula (which has an outside diameter smaller than the inside diameter of a conduit 81 through the nozzle), and disk toward the outlet end of the valve until the disk seats on an inwardly facing annular shoulder 82 of bore 22. The second cover is restrained by the tapered shoulder 74 from moving toward the valve outlet. Thus, the shoulder 82 and the tapered shoulder 74 differentially limit the travel of the disk and second cover toward the valve outlet. Continued movement of the tapered element 80 until it fits snugly in the tapered socket 40 (as shown in FIG. 2) causes the first cover to move inwardly and longitudinally relative to the cannula, which pierces the first rubber cover. The cannula also moves longitudinally relative to the outer end of the second cover (which is restrained by tapered shoulder 74 from moving toward the outlet) and pierces it so the fluid passageway 56 through the cannula is open for fluid flow in either direction, depending on whether medication (not shown) is to be administered to the patient, or a blood sample is to be withdrawn by aspiration from the patient. In either event, the inner end of tubular element 80 makes a fluidtight seal against the outer end of the first cover during flow of fluid through the cannula. The outer end of the second cover makes a fluidtight seal in tapered shoulder 74. Accordingly, the flow path for fluids is limited to passageway 56 extending through the cannula.

The increased wall thickness of the covers adjacent their respective outer ends ensures good contact between the nozzle 80 and the first cover, and between the tapered shoulder 76 and the second cover.

A pair of outwardly extending ears 84, formed integrally with the inlet end of valve body section 18, are provided for locking the tubular element 80 in the tapered socket 40, if the tubular element carries a Luer-lock collar of the type provided around the outlet end of valve body section 24.

As shown in FIG. 2, each of the rubber covers are compressed and distorted so that they are the equivalent of springs in compression. After the tubular element 80 is removed from the tubular socket 40, the rubber covers expand to their original respective positions shown in FIG. 1, moving the disk upwardly (as viewed in FIGS. 1 and 2) until the annular rubber flange 66 bears against the inner end 19 of valve body section 18. The outer periphery of rubber flange 66 makes a sliding seal against bore 22 so that the annular space surrounding the first cover is always sealed from the annular space surrounding the second cover.

When the valve returns to its closed position shown in FIG. 1, the resilient, elastomeric covers immediately reseal and prevent any contamination of the cannula interior. Moreover, the outer end of the first cover terminates a relatively short distance within the inlet end of the valve body so the out end of the first cover can easily be reached for swabbing it with alcohol to sterilize the cover before use.

The maximum diameter of the tapered socket 40 and the distance from the sharp end of the cannula to the outer end of valve body section 18 is such that the user of the device cannot accidentally be stuck by the cannula. The same is true with respect to the diameter of bore 16 and the distance from the second sharp end of the cannula to the outer end of bore 16, even when the valve is in the open position shown in FIG. 2.

With the valve in the position shown in FIG. 1, the second cover is in slight compression so that it is held firmly against the tapered shoulder 74. Thus, if the patient to whom the intermittent cap or valve is connected should cough, or otherwise create a momentary pressure surge, undesired backflow is prevented by the outer end of the second cover sealing the opening surrounded by tapered shoulder 74. In the unlikely event that the pressure surges high enough to displace the second cover in an inward direction, the sliding seal made by the flange on the first cover against the bore 22 and the seal made by that flange against inner end 19 of valve body section 18 prevents the flow of any fluid into the annular space surrounding the first cover.

As can be seen from the foregoing description, even if the inlet end of the valve is left open while it is not in use, any contaminants entering the valve inlet are excluded from the cannula interior by the first cover, which can easily be sterilized before use. Moreover, any contaminants which may find their way into the annular space surrounding the first cover are excluded by rubber flange 66 from the annular space around the second cover. Thus, the flow path for fluids through the valve is kept sterile.

I claim:

1. A self-sealing valve insert comprising:
    an elongated cannula having first and second shap ends; and
    first and second elongated, flexible, resilient, elastomeric covers each disposed respectively over the first and second sharp ends of the cannula, each cover being secured to an intermediate portion of the cannula to provide a closed envelope over a respective adjacent sharp end of the cannula, and made of a material which is penetrable by the sharp ends of the cannula;
    each cover, from where it is over a respective adjacent shape end of the cannula to a point adjacent where each cover is secured to the cannula, making a loose fit around the cannula so when a force is applied to the covers to move them relative to the cannula and toward each other, the covers are compressed, and each is penetrated by the respective adjacent sharp end of the cannula, and so when force is removed, each cover is free to expand back to its original rest position to form a seal over a respective adjacent sharp end of the cannula.

2. A valve insert according to claim 1 which includes a disk secured around an intermediate part of the cannula exterior, and in which each cover is secured to the disk.

3. A valve insert according to claim 2 in which the disk includes a first hub extending toward the first sharp end of the cannula, and a second hub extending toward the second sharp end of the cannula, and the first and second covers each respectively make a tight stretch fit over the first and second hubs.

4. A valve insert according to claim 3 in which each hub includes an outwardly extending barb to engage the cover stretched over it.

5. A valve insert according to claim 2, 3, or 4 in which at least one of the covers includes an outwardly extending annular flange which fits against the disk.

6. A valve insert according to claim 5 in which the annular flange extends outwardly from the cannula farther than the disk.

7. A valve insert according to claim 1, 2, 3, or 4 in which the thickness of at least one cover adjacent a sharp end of the cannula is less than the thickness of an adjacent part of the cover.

8. A valve insert according to claim 5 in which the thickness of at least one cover adjacent a sharp end of the cannula is less than the thickness of an adjacent part of the cover.

9. A valve comprising:
    an elongated body with a bore extending longitudinally through it to form an inlet at one end of the body and an outlet at the other end of the body;
    an elongated cannula disposed in the bore to be movable longitudinally relative to the body, the cannula having first and second sharp ends respectively disposed adjacent the inlet and the outlet;
    first and second elongated, flexible, resilient, elastomeric covers respectively disposed over the first and second sharp ends of the cannula, each cover being secured to an intermediate part of the cannula to form a separate respective closed envelope over a respective sharp end, the covers being made of a material penetrable by the sharp ends; and
    means for limiting the travel of the cannula and the second cover in a direction toward the outlet when a tubular element enters the inlet and pushes the first cover and cannula toward the outlet and cause each sharp point to penetrate the respective surrounding cover.

10. A valve according to claim 9 which includes means for differentially limiting the travel of the cannula and the second cover in a direction toward the outlet.

11. A valve according to claim 9 which includes a disk secured around an intermediate part of the cannula exterior, and in which each cover is secured to the disk.

12. A valve according to claim 11 in which the disk includes a first hub extending toward the first sharp end of the cannula, and a second hub extending toward the second sharp end of the cannula, and the first and second covers each respectively make a stretch fit over the first and second hubs.

13. A valve according to claim 12 in which each hub includes an outwardly extending barb to engage the cover stretched over it.

14. A valve according to claim 11, 12, or 13 in which the disk makes a close sliding fit in the bore through the body to position the cannula substantially coaxially in the bore.

15. A valve according to claim 11, 12, or 13 which includes a first internal shoulder in the bore to limit the travel of the disk toward the inlet end of the bore.

16. A valve according to claim 11, 12, or 13 which includes a tapered shoulder in the bore for engaging the end of the second cover disposed over the second sharp point of the cannula and thus limit the travel of the second cover in a direction toward the bore outlet.

17. A valve according to claim 11, 12, or 13 which includes a second internal shoulder which limits the travel of the disk toward the inlet end of the bore.

18. A valve according to claim 11, 12, or 13 which includes an outwardly extending rubber flange on the first cover.

19. A valve according to claim 18 in which the rubber flange makes a sliding seal in the bore as the first cover moves longitudinally in the bore.

20. A valve according to claim 9, 10, 11, 12, or 13 in which the inlet end of the bore projects longitudinally beyond the first sharp end of the cannula.

21. A valve according to claim 9, 10, 11, 12, or 13 in which the outlet end of the bore extends longitudinally beyond the second sharp end of the cannula.

22. A valve according to claim 20 in which the outlet end of the bore extends longitudinally beyond the second end of the cannula.

23. A valve insert according to claim 9, 10, 11, 12, or 13 in which the thickness of at least one cover adjacent a sharp end of the cannula is less than the thickness of an adjacent part of the cover.

* * * * *